United States Patent
Gu et al.

(10) Patent No.: US 10,829,497 B2
(45) Date of Patent: Nov. 10, 2020

(54) CRYSTAL FORM II OF THIENOPYRIDINE DERIVATIVE BISULFATE AND PREPARATION METHOD THEREFOR AND USE THEREOF

(71) Applicant: ZHONGRONG KAITE (BEIJING) BIOTECHNOLOGY CO., LTD., Beijing (CN)

(72) Inventors: Jingkai Gu, Beijing (CN); Xueyu Xu, Beijing (CN); Hao Wang, Beijing (CN); Xue Zhao, Beijing (CN)

(73) Assignee: ZHONGRONG KAITE (BEIJING) BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/639,113

(22) PCT Filed: Jun. 25, 2018

(86) PCT No.: PCT/CN2018/092635
§ 371 (c)(1),
(2) Date: Feb. 13, 2020

(87) PCT Pub. No.: WO2019/033850
PCT Pub. Date: Feb. 21, 2019

(65) Prior Publication Data
US 2020/0207781 A1  Jul. 2, 2020

(30) Foreign Application Priority Data
Aug. 16, 2017 (CN) .......................... 2017 1 0700262

(51) Int. Cl.
*C07D 495/04* (2006.01)
(52) U.S. Cl.
CPC ........ *C07D 495/04* (2013.01); *C07B 2200/13* (2013.01)
(58) Field of Classification Search
CPC .......................... C07D 495/04; A61K 31/4365
USPC ........................................... 546/114; 514/301
See application file for complete search history.

(56) References Cited

FOREIGN PATENT DOCUMENTS

| CN | 102796114 A | 11/2012 |
|---|---|---|
| CN | 102924474 A | 2/2013 |
| CN | 103554132 A | 2/2014 |
| CN | 103554132 B | 1/2016 |
| CN | 107337683 A | 11/2017 |
| WO | 2008157563 A2 | 12/2008 |

OTHER PUBLICATIONS

Xu, Xueyu et al, "Significant Improvement of Metabolic Characteristics and Bioactivities of Clopidogrel and Analogs by Selective Deuteration" Journal of Molecules, vol. 21, No. 6, (Jun. 21, 2016).
The International Search Report of corresponding International application No. PCT/CN2018/092635, dated Sep. 30, 2018.
The Chinese First Examination Report and the Search Report of corresponding Chinese application No. 201710700262.2, dated Oct. 31, 2018.

*Primary Examiner* — Charanjit Aulakh
(74) *Attorney, Agent, or Firm* — J.C. Patents (57) ABSTRACT

Disclosed are a crystal form II of a thienopyridine derivative bisulfate and a preparation method therefor and the use thereof. The X-ray powder diffraction pattern of the crystal form II represented by the 2θ diffraction angle exhibits characteristic diffraction peaks at 12.86°, 13.58°, 15.58°, 17.64°, 18.42°, 21.56°, 22.90°, 23.70° and 24.64°. The crystal form can be used as an active ingredient for preparing a pharmaceutical composition for preventing and treating diseases caused by thrombi. Compared with the original crystal form, the crystal form II of the invention has a better stability, with denser bulk solid particles, and is less susceptible to static electricity, and has better fluidity and compressibility, and when used as an active ingredient for preparing a pharmaceutical composition, the pharmaceutical preparation prepared with the crystal form II has a stronger stability.

11 Claims, 8 Drawing Sheets

CRYSTAL FORM II OF THIENOPYRIDINE DERIVATIVE BISULFATE AND PREPARATION METHOD THEREFOR AND USE THEREOF

CROSS-REFERENCE TO RELATED APPLICATION

This application is a national phase application of international application No. PCT/CN2018/092635 filed on Jun. 25, 2018, which in turn claims the priority benefits of Chinese application No. 201710700262.2, filed on Aug. 16, 2017. The contents of these prior applications are hereby incorporated by reference in their entirety.

TECHNICAL FIELD

The invention relates to the field of medicine, in particular to a novel crystalline form of thienopyridine derivative, its preparation and application thereof.

BACKGROUND OF INVENTION

The thienopyridine derivative of formula I (hereinafter referred to as the compound of formula I), the chemical name is Methyl-d$_3$ (2S)-2-(2-chlorophenyl)-2-(6,7-dihydrothieno[3,2-c]pyridin-5(4H)-yl)acetate can be used to prevent and treat heart, brain and other arterial circulation disorders caused by high platelet aggregation, such as recent stroke, myocardial infarction and diagnosed peripheral arteries disease.

Formula I

WO2008157563A2 disclosed the compound of formula I and a pharmaceutically acceptable salt thereof (including hydrogen sulfate), which can be used for preparing medicine for treating coronary artery disease, peripheral vascular disease and cerebrovascular disease, without disclosing the preparation method and crystal characteristics of any salt thereof (including hydrogen sulfate).

CN201310533062.4 also disclosed the compound of formula I and a pharmaceutically acceptable salt thereof, and specifically disclosed a method for preparing a hydrogen sulfate, namely by adding the compound of formula I to acetone, stirring and dissolving, cooling in ice bath, dropwise adding sulfuric acid and continuing stirring for 2 hours, crystals precipitated gradually, filtering the crystals and drying to obtain a hydrogen sulfate of the compound of formula I as a white solid powder, but without disclosing any crystal characteristics.

Xu et al. (Molecules 2016, 21, 704) disclosed adding sulfuric acid to the acetonic solution of the compound of formula I, cooling to 0° C., stirring for 2 hours, filtering the precipitated crystals, recrystallizing with water and acetone, acquired a white crystal powder of the hydrogen sulfate of the compound of formula I, only the melting point was measured at 177.3-178.2 (uncorrected) and there was no accurate description about the crystal form.

In case a drug has more than one crystalline form, it is called polymorphism. As we all know, different crystal forms of the same drug usually show different physical properties and chemical stability. Therefore, the use of an active pharmaceutical ingredient with definite crystalline form for the formulation production has an important role in ensuring the efficacy of the drug and reducing the incidence of toxic and side effects. So far, there is no definite crystalline form study of the hydrogen sulfate of the compound of formula I, which cannot provide more qualitative and quantitative information for the study of solid drugs. Therefore, it is of great significance to develop a stable crystalline form of the hydrogen sulfate of the compound of formula I suitable for use in pharmaceutical compositions.

CONTENT OF THE INVENTION

The aim of the present invention is to provide a novel crystalline form of the hydrogen sulfate of the compound of formula I, namely the form II. The other aim of the present invention is to provide a preparation method for the hydrogen sulfate form II of the compound of formula I. A further aim of the present invention is to provide the medicinal use of the hydrogen sulfate crystalline form II of the compound of formula I, specifically to prevent and treat diseases caused by thrombus by inhibiting platelet aggregation. The object of the present invention was achieved by the following technical solutions.

The hydrogen sulfate crystalline form II of the compound of formula I provides characteristic X-ray powder diffraction peaks at 2θ angle values of 12.86°, 13.58°, 15.58°, 17.64°, 18.42°, 21.56°, 22.90°, 23.70°, 24.64°, with an error range about ±0.2°.

Formula I

The described hydrogen sulfate crystalline form II of the compound of formula I provides characteristic infrared absorption peaks at wavenumbers (/cm$^{-1}$) of 2509, 1751, 1254, 1190, 1154, 1058, 869, 777 and 567; it has a peak value of the differential scanning calorimetry chart at 179.3° C. and melting enthalpy of 89.2 J/g.

The deuterium atom content of the deuterated methyl group in the compound of the present invention is not less than 50%, preferably not less than 70%, and most preferably not less than 90%.

The invention also provides the following preparation method:

Method 1: In the present invention, the compound of formula I was added to acetone, dissolved by stirring, cooled in ice bath, added sulfuric acid dropwise, stirred for crystallization and filtered to obtain the hydrogen sulfate form I of the compound of formula I. The filtered mother liquor was set in cold storage room below 10° C. (preferably below 4° C.) for more than 1 month (preferably more than 2 months), a new the hydrogen sulfate crystal form of the compound of formula I was obtained, namely the crystal form II, characterized in that: the X-ray powder diffraction pattern is clearly shown in FIG. 4, it provides peaks at 2θ angle values of 12.86°, 13.58°, 15.58°, 17.64°, 18.42°, 21.56°, 22.90°, 23.70°, 24.64°; the infrared absorption spectrum is clearly shown in FIG. 5, gives peaks at 2509, 1751, 1254, 1190, 1154, 1058, 869, 777, 567 cm$^{-1}$; has a peak value of the differential scanning calorimetry chart (FIG. 6) at 179.3° C., and melting enthalpy of 89.2 J/g.

Method 2: Adding the compound of formula I to a ketonic solvent or a ketonic solvent combination including, but not limited to one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, dissolving by stirring, adding sulfuric acid, heating to reflux and keeping refluxing, crystals precipitated gradually, then cooling, stirring, filtering and drying to obtain the hydrogen sulfate crystal form II of the compound of formula I.

Method 3: Adding the compound of formula I to a ketonic solvent or a ketonic solvent combination including, but not limited to one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, dissolving by stirring, adding sulfuric acid, heating to reflux and keeping refluxing, crystals precipitated gradually, removing portion of solvents by distillation then cooling, stirring, filtering and drying to obtain the hydrogen sulfate crystal form II of the compound of formula I.

Method 4: Adding the compound of formula I to a ketonic solvent or a ketonic solvent combination including, but not limited to one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve, adding sulfuric acid, adding crystal seeds of the hydrogen sulfate crystalline form II of the compound of formula I, stirring and crystals precipitated gradually, filtering and drying to obtain the hydrogen sulfate crystal form II of the compound of formula I.

Method 5: Adding the compound of formula I to a ketonic solvent or a ketonic solvent combination including, but not limited to one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve, adding sulfuric acid, adding crystal seeds of the hydrogen sulfate crystalline form II of the compound of formula I, crystals precipitated gradually, removing portion of solvents by distillation then cooling, stirring, filtering and drying to obtain the hydrogen sulfate crystal form II of the compound of formula I.

Crystals are solid substances composed of atoms (or ions, molecules) arranged periodically in space. The crystals of organic drugs basically belong to molecular lattice. Different crystal forms are produced under different process conditions. Different crystal forms of the same drug often cause significant differences in the physicochemical properties of the drug in appearance, solubility, melting point, density, etc., as well as drug dissolution, bioavailability, etc., thereby affecting the effectiveness of drug stability, bioavailability and other effects. Drug polymorphism study has become an indispensable part in the development and approval of new drugs, as to the production and quality control of drugs and design of novel drug formulations.

The beneficial effects of the present invention:

The results of stability studies under high temperature and high humidity conditions (see example 3 for details) showed that the crystalline form II of the present invention has better stability than the crystalline form I of the hydrogen sulfate of the compound of formula I.

The hydrogen sulfate of the compound of formula I having the crystal form II provided by the present invention can be used for preparation of a pharmaceutical composition for preventing and treating diseases caused by thrombosis. Compared with form I, form II is more stable, more compact bulk solid particles and less susceptible to static electricity, better fluidity and compressibility, which is more suitable as API for the preparation of pharmaceutical compositions and brings great convenience for the practical formulation production.

DETAILED DESCRIPTION

In order to develop crystal forms of the hydrogen sulfate of the compound of formula I suitable for pharmaceutical composition, the hydrogen sulfate crystals of the compound of formula I were prepared according to the methods disclosed by CN201310533062.4 and Xu et al. respectively, it was found the obtained crystals provided the same crystalline characteristics, namely crystalline form I. The present invention further discovered a novel crystal form of the hydrogen sulfate of the compound of formula I, namely the form II, is significantly different from the form I in physical properties, such as X-ray powder diffraction and infrared absorption spectrum.

Compared with the hydrogen sulfate crystalline form I of the compound of formula I, the crystalline form II of the present invention has better stability, more compact bulk solid particles, less susceptible to static electricity, better fluidity and compressibility, so it is more adaptable as an active ingredient for the preparation of a pharmaceutical composition, to achieve a better stability of drug formulation.

The powder X-ray diffraction measurement of the hydrogen sulfate of the compound of formula I with the crystalline form I and II prepared by the present invention was performed on a Rigaku D/max2500 X-ray diffractometer (CuK$_\alpha$λ=1.5405 Å), and the infrared absorption measurement was performed on a Perkin Elmer Spectrum 400. A Fourier transform infrared spectrometer (potassium bromide tablet) was performed, and a differential scanning thermal analysis was performed on a METTLERTOLEDO DSC 3+ differential scanning calorimeter (temperature increase rate: 10° C./min).

Figure 1:
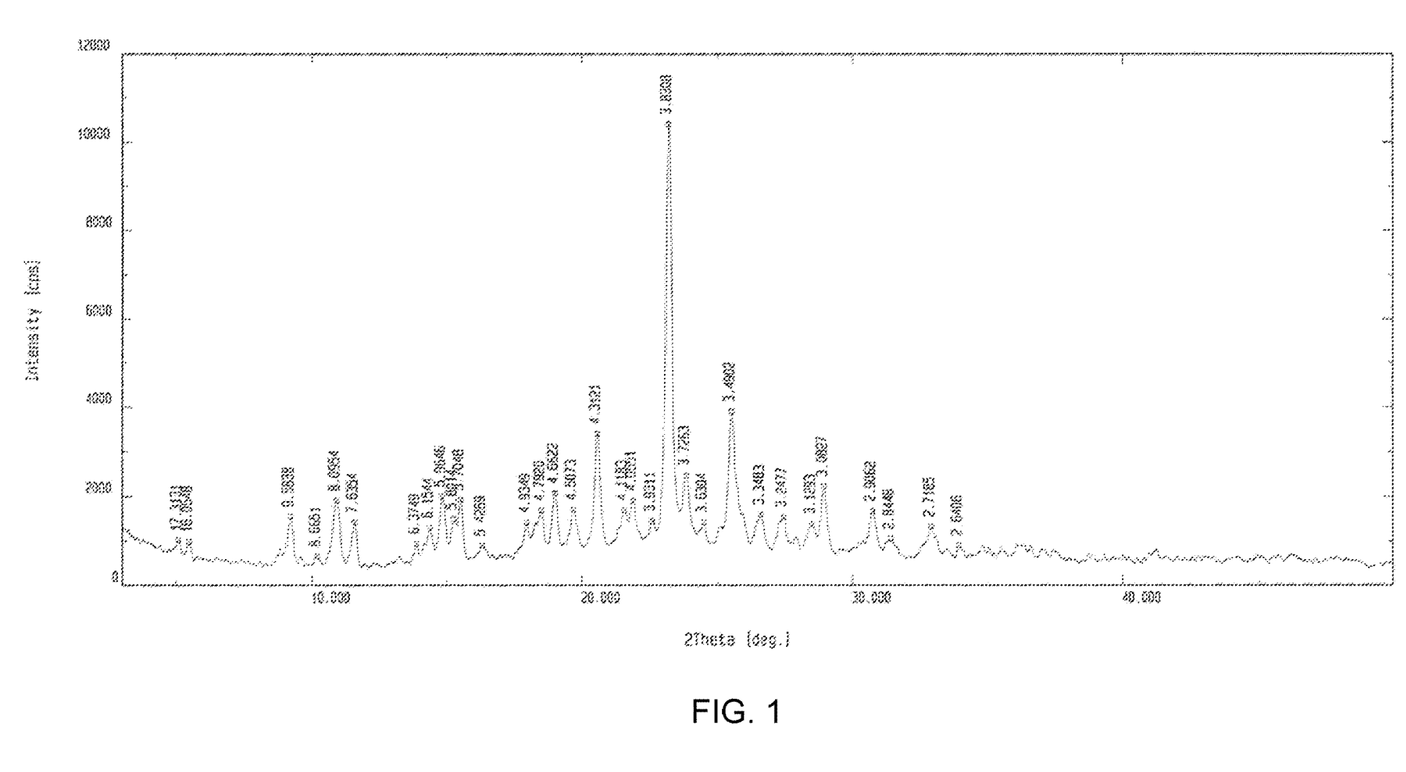
FIG. 1 is the powder X-ray diffraction pattern of the hydrogen sulfate form I of the compound of formula I.
Figure 2:
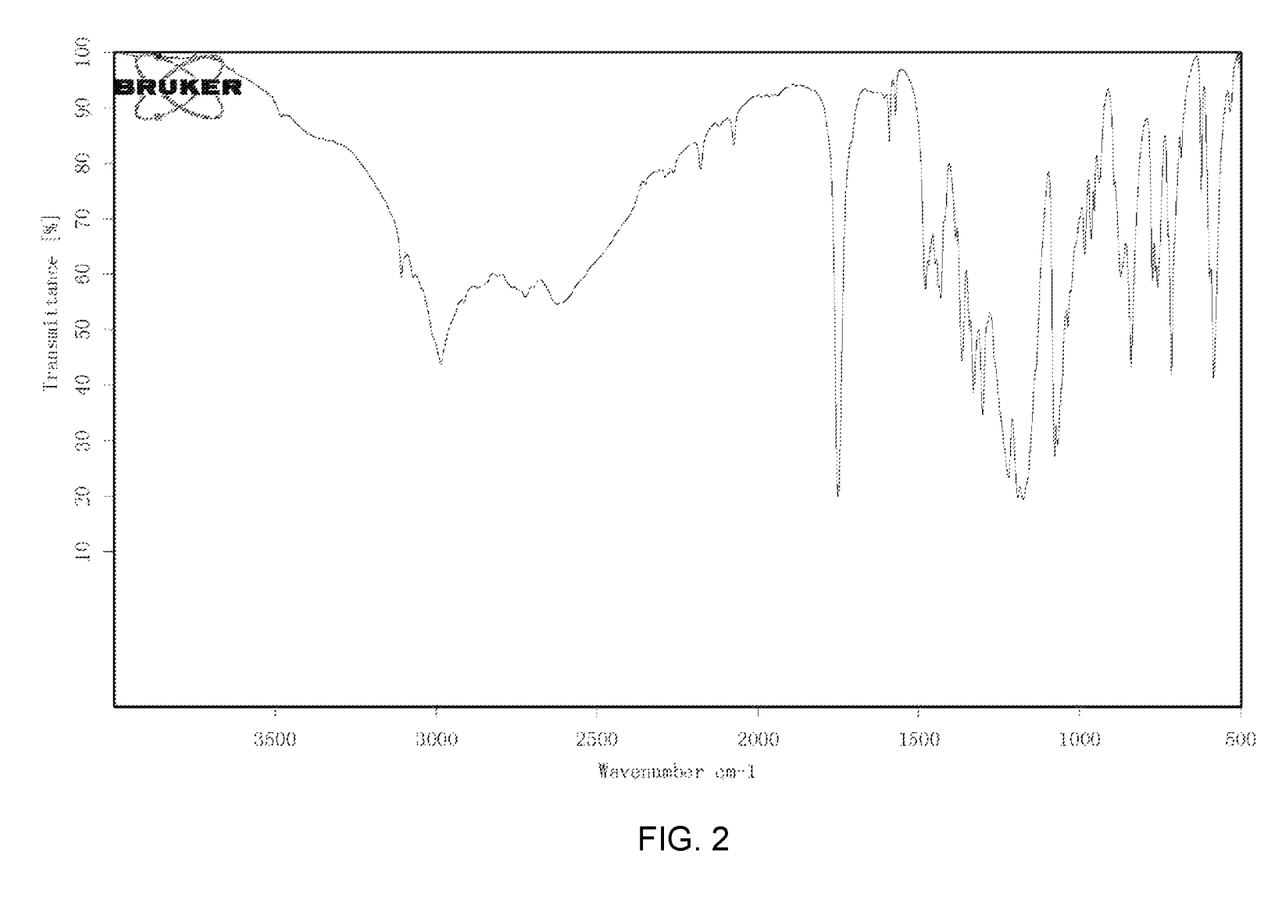
FIG. 2 is the infrared absorption spectrum of the hydrogen sulfate form I of the compound of formula I.
Figure 3:
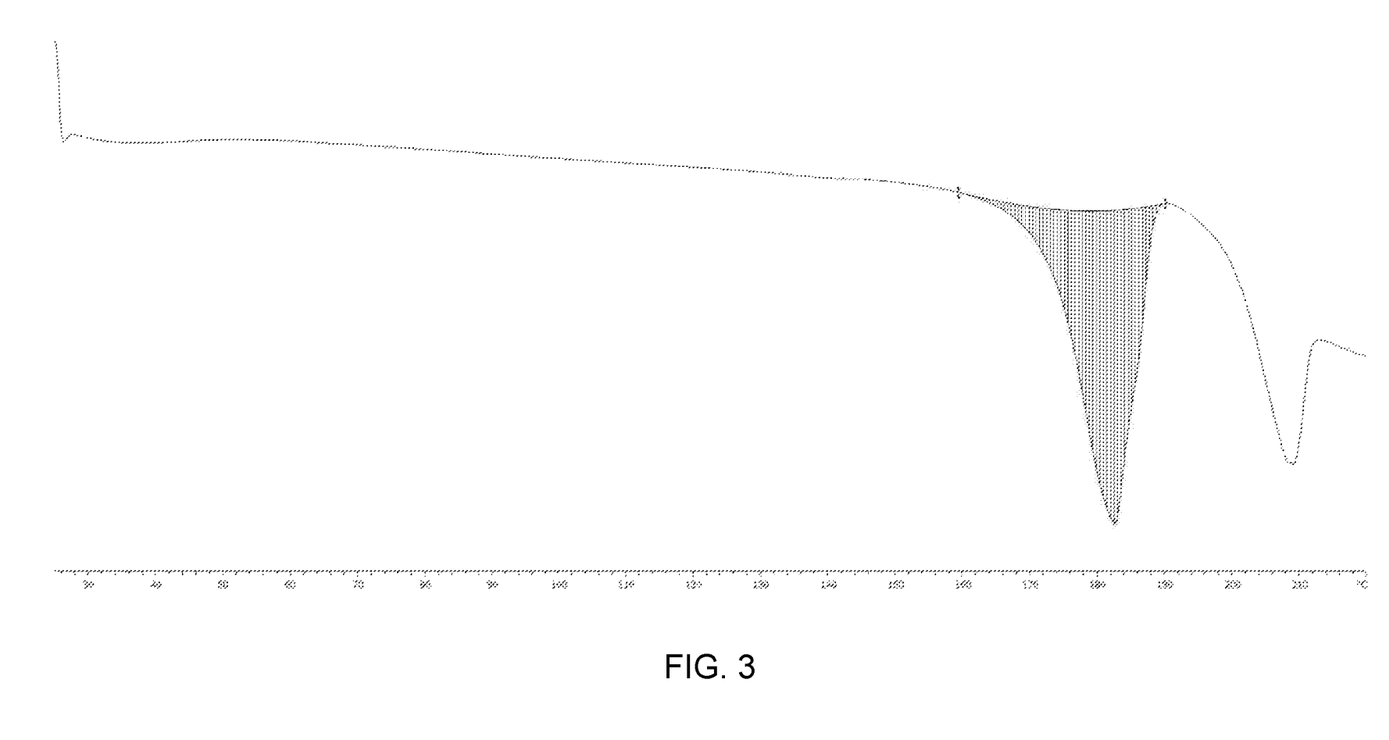
FIG. 3 is the differential scanning thermal analysis chart of the hydrogen sulfate form I of the compound of formula I.

The prepared hydrogen sulfate crystalline of the compound of formula I according to the method disclosed by CN201310533062.4 or Xu et al provided the same crystal form characteristics, namely crystalline form I. Its X-ray powder diffraction pattern is clearly shown in FIG. 1 and has peaks at 2θ angles of 9.22°, 10.92°, 11.58°, 14.84°, 19.02°, 20.58°, 23.20°, 23.86°, 25.50°, with an error range of ±0.2°. Its infrared absorption spectrum is clearly shown in FIG. 2, with peaks at 2986, 1753, 1220, 1175, 1077, 840, 716 cm−1; the peak of differential scanning thermal analysis (FIG. 3) is 182.4° C., the melting enthalpy is 62.7 J/g.

Figure 7:
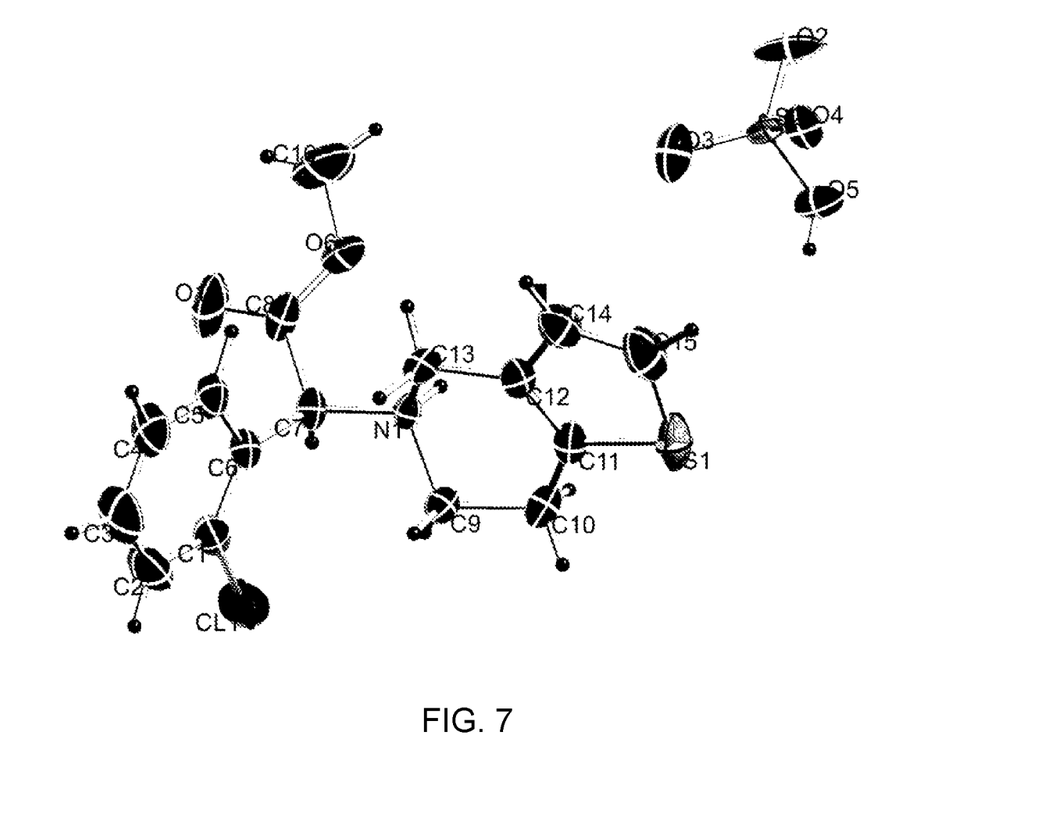
FIG. 7 is the crystal structure of the hydrogen sulfate form II of the compound of formula I.
Figure 8:
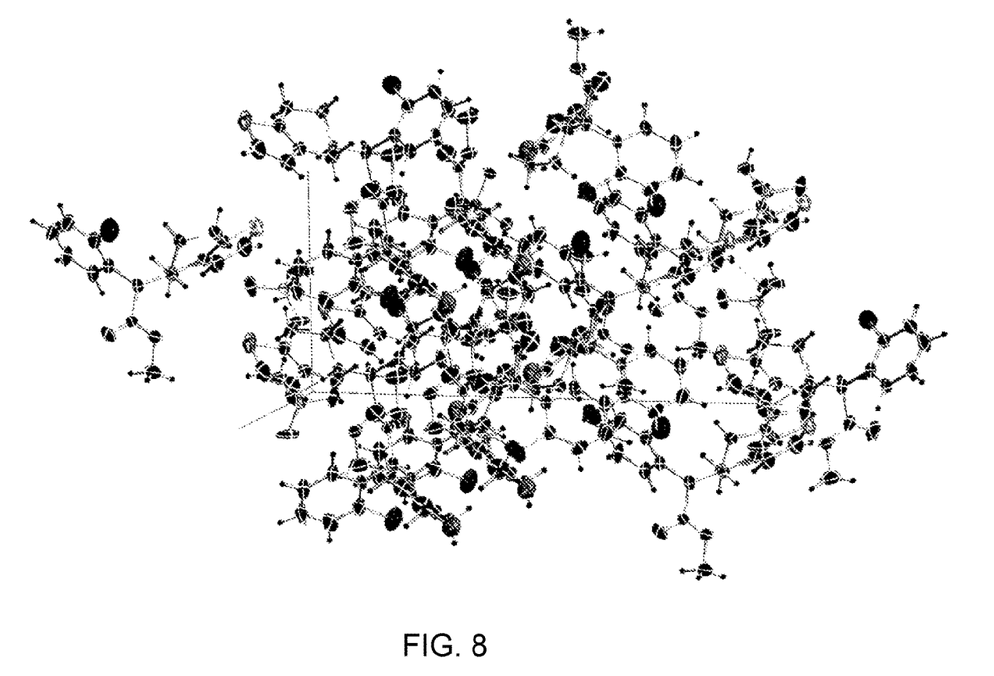
FIG. 8 is the crystal cell packing diagram of the bisulfate crystal form II of the compound of formula I.

The obtained hydrogen sulfate crystal form II of the compound of formula I was characterized by X-ray single crystal diffraction on a BRUKER D8VENTURE X-ray single crystal diffractometer (CuK$_\alpha$ radiation), and the crystal structure was analyzed by direct method (shelxs-97). All non-hydrogen atom positions were obtained, structural parameters were modified by least squares method to discriminate atom types, all hydrogen atom positions were obtained by geometric calculation method and difference Fourier method, the final reliability factors $R_1$=0.0331, $wR_2$=0.0846, S=1.043, The Flack factor is 0.1089 (0.0153), and its molecular three-dimensional structure diagram and crystal cell packing diagram are clearly shown in FIGS. 7 and 8. The crystal of the hydrogen sulfate crystal form II of the compound of formula I is colorless columnar, belonging to an orthorhombic system, the space group is $P2_12_12_1$, and the crystal cell parameters: a=9.1711(14)Å, b=10.3433(15)Å, c=20.1015(29)Å, α=90°, β=90°, γ=90°, cell volume V=1906.82 Å$^3$.

Figure 4:
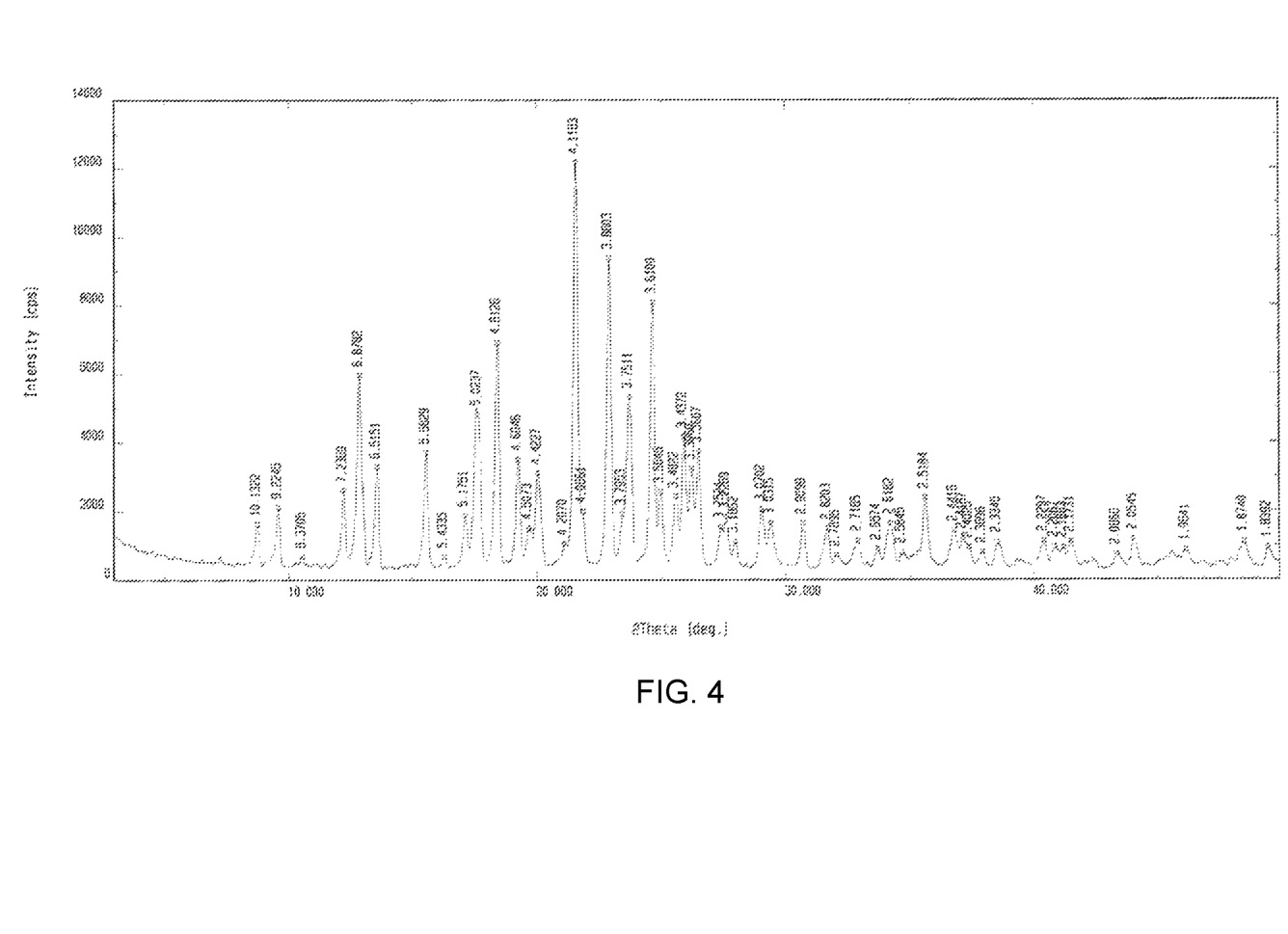
FIG. 4 is the powder X-ray diffraction pattern of the hydrogen sulfate form II of the compound of formula I.
Figure 5:
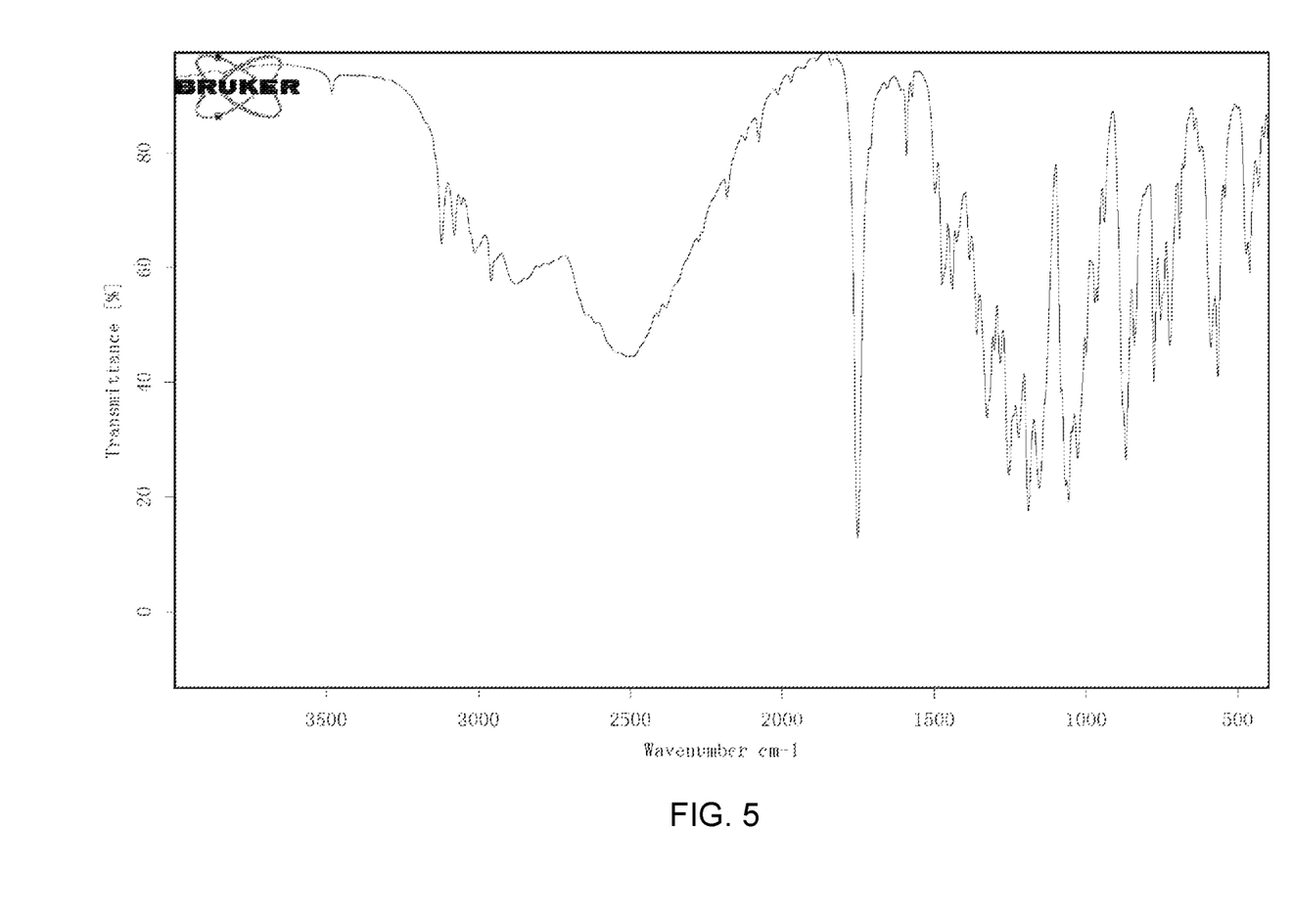
FIG. 5 is the infrared absorption spectrum of the hydrogen sulfate form II of the compound of formula I.
Figure 6:
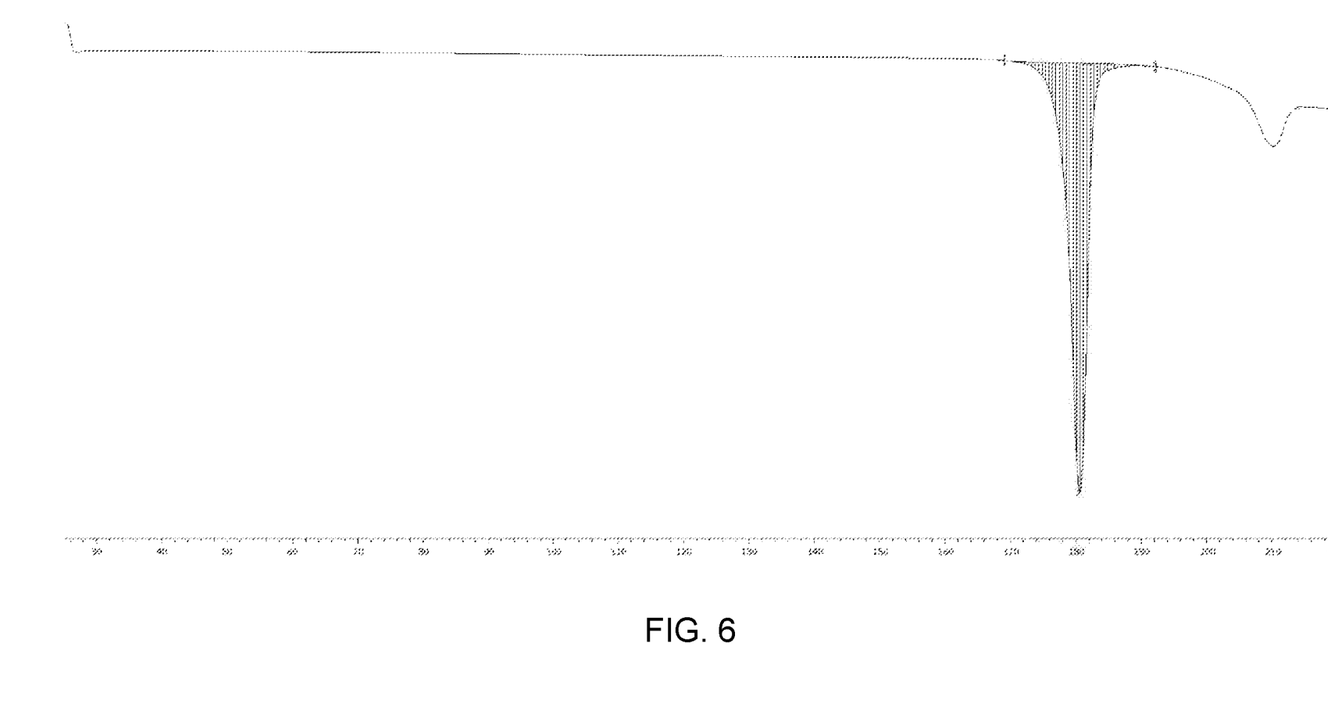
FIG. 6 is the differential scanning thermal analysis chart of the hydrogen sulfate form II of the compound of formula I.

The X-ray powder diffraction pattern of the hydrogen sulfate form II of the compound of formula I is clearly shown in FIG. 4 with peaks at 2θ angles of 12.86°, 13.58°, 15.58°, 17.64°, 18.42°, 21.56°, 22.90°, 23.70° and 24.64°; infrared absorption spectrum is clearly shown in FIG. 5 with peaks at 2509, 1751, 1254, 1190, 1154, 1058, 869, 777, 567 cm$^{-1}$; differential scanning thermal analysis spectrum (FIG. 6) with peak at 179.3° C., and the melting enthalpy is 89.2 J/g.

Test Example 1

Preparation of Hydrogen Sulfate Crystal Form I of the Compound of Formula I

According to the method in CN201310533062.4 Example 5, adding the compound of formula I (20.0 g) to acetone (100 mL), stirring to dissolve, cooling in ice bath, adding sulfuric acid (6.16 g) dropwise, continue stirring for 2 hours, crystals precipitated gradually, filtering and drying at 50° C. under vacuum to obtain the hydrogen sulfate form I of the compound of formula I (20.6 g). Its X-ray powder diffraction pattern has peaks at 2θ angles of 9.22°, 10.92°, 11.58°, 14.84°, 19.02°, 20.58°, 23.20°, 23.86°, 25.50°. Its infrared absorption spectrum has peaks at 2986, 1753, 1220, 1175, 1077, 840, 716 cm$^{-1}$; the peak of differential scanning thermal analysis is 182.4° C., the melting enthalpy is 62.7 J/g.

Test Example 2

Preparation of Hydrogen Sulfate Crystal Form I of the Compound of Formula I

According to the method by Xu et al., the hydrogen sulfate (1.00 g) of the compound of formula I obtained from the test example 1 was added to a water-acetone mixture (23 mL, volume ratio 1:5), heated to reflux, the solids were dissolved, cooled to 0° C. and stirred for 2 hours. The precipitate was filtered and dried under vacuum at 60° C. to obtain the hydrogen sulfate form I (0.62 g) of the compound of formula I. Its X-ray powder diffraction pattern has peaks at 2θ angles of 9.06°, 10.80°, 11.44°, 14.72°, 18.86°, 20.46°, 23.08°, 23.74°, 25.36°. Its infrared absorption spectrum has peaks at 2986, 1753, 1220, 1174, 1077, 840, 715 cm$^{-1}$; the peak of differential scanning thermal analysis is 181.7° C., the melting enthalpy is 57.2 J/g.

Test Example 3

Stability Study of the Hydrogen Sulfate Crystal Form I and Form II of the Compound of Formula I Under High Temperature and High Humidity Conditions Setting the hydrogen sulfate crystal form I and form II of the compound of formula I at temperature of 60° C. and high humidity (25° C., relative humidity of 90%±5%) respectively for 10 days. Samples were taken on the 0, 5th and 10th days and determined by high performance liquid chromatography to investigate the changes in impurities.

Chromatographic conditions: Agilent 1100 for high performance liquid chromatography; chromatographic column ULTRON ES-OVM (5 μm, 4.6 mm×150 mm); mobile phase 0.01 mol/L potassium dihydrogen phosphate aqueous solution-acetonitrile (80:20); detection wavelength 220 nm; column temperature 30° C.; flow rate 1.0 mL/min; injection volume 10 μL.

Test method: accurately weighting 5 mg of the test probe, placing it in a 10 mL volumetric flask, adding 1 mL of methanol, dissolving with ultrasound, diluting to the mark with mobile phase and shaking to make a test solution with a concentration of 0.5 mg/mL. Precisely injecting 10 μL of the test solution into the liquid chromatography, recording the chromatogram and calculating the total content of impurities according to peak area normalization method.

The results of the stability test under high temperature and high humidity conditions are shown in Table 3. The results show that, compared with the hydrogen sulfate form I of the compound of formula I, the total impurity growth rate of form II is lower and has better stability.

TABLE 3

Stability test results under high temperature and high humidity conditions

| Conditions | Crystal Form | Total Impurity Content (peak area %) | | | Total Impurity Growth Rate |
|---|---|---|---|---|---|
| | | 0 day | 5$^{th}$ day | 10$^{th}$ day | |
| High Temperature | I | 0.386 | 0.597 | 0.812 | 110% |
| | II | 0.372 | 0.526 | 0.737 | 98.1% |
| High Humidity | I | 0.386 | 0.438 | 0.576 | 49.2% |
| | II | 0.372 | 0.409 | 0.533 | 43.3% |

The present invention is further described below through specific embodiments, but is not intended to limit the present invention.

Embodiment 1

Preparation of the Hydrogen Sulfate Crystal Form II of the Compound of Formula I The filtrate in test example 1 was placed in a refrigerator at 4° C., left for 2 months, crystals were precipitated, and filtered to obtain 0.32 g of crystals of the hydrogen sulfate salt form II of the compound of formula I.

Embodiment 2

Preparation of the Hydrogen Sulfate Crystal Form II of the Compound of Formula I The compound of formula I (5.03 g) is added to acetone (40 mL), stirred to dissolve, added 80% sulfuric acid (2.02 g), heated to reflux and maintained reflux for 2 hours, crystals precipitated gradually, cooled to room temperature, and continued stirring for 4 hours, filtered and dried under vacuum at 50° C. to obtain 4.98 g of hydrogen sulfate salt form II of the compound of formula I (yield: 76.1%).

Embodiment 3

Preparation of the Hydrogen Sulfate Crystal Form II of the Compound of Formula I The compound of formula I (5.11 g) is added to acetone (50 mL), stirred to dissolve, added 98% sulfuric acid (1.63 g), heated to reflux and kept refluxing for 2 hours, crystals precipitated gradually, cooled to room temperature, removes the solvent by distillation and remains about ⅓ of the volume, cooled to −5 to 0° C. and continued stirring for 4 hours, filtered, and dried under vacuum at 50° C. to obtain 6.24 g of hydrogen sulfate salt form II of the compound of formula I (yield 93.8%).

Embodiment 4

Preparation of the Hydrogen Sulfate Crystal Form II of the Compound of Formula I The compound of formula I (3.67 g) is added to methyl ethyl ketone (37 mL), stirred to dissolve, added 98% sulfuric acid (1.15 g), heated to reflux and maintained reflux for 2 hours, crystals precipitated gradually, cooled to −10~−5° C., continued stirring for 4 hours, filtered, and dried under vacuum at 50° C. to obtain 4.08 g of hydrogen sulfate salt form II of the compound of formula I (yield: 85.4%).

Embodiment 5

Preparation of the Hydrogen Sulfate Crystal Form II of the Compound of Formula I The compound of formula I (20.1 g) is added to acetone (160 mL), stirred to dissolve, added 98% sulfuric acid (6.24 g), seed crystals (0.012 g) of hydrogen sulfate salt form II of the compound of formula I is added, stirred for 2 hours, crystals precipitated gradually and the mixture is stirred at −5 to 0° C. for 4 hours, filtered, and dried under vacuum at 50° C. to obtain 23.4 g of hydrogen sulfate salt form II of the compound of formula I (yield: 89.4%).

Embodiment 6

Preparation of the Hydrogen Sulfate Crystal Form II of the Compound of Formula I The compound of formula I (20.0 g) is added to 2-pentanone (210 mL), stirred to dissolve, added 98% sulfuric acid (6.16 g) dropwise, added seed crystals (0.015 g) of bisulfate form II of the compound of formula I, crystals precipitated gradually, filtered and dried under vacuum at 60° C. to obtain 21.2 g (yield 81.4%) of the hydrogen sulfate salt form II of the compound of formula I.

Embodiment 7

Preparation of the Hydrogen Sulfate Crystal Form II of the Compound of Formula I The compound of formula I (4.89 g) is added to cyclohexanone (80 mL). After dissolving, 80% sulfuric acid (1.86 g) was added, heated at 60-65° C., stirred at 0-5° C., filtered, and dried at 65° C. under vacuum to obtain the hydrogen sulfate salt form II, 5.52 g (86.7% yield) of the compound of formula I.

What is claimed is:

1. A hydrogen sulfate crystalline form II of the compound of formula I, characterized in that it provides characteristic X-ray powder diffraction peaks at 2θ angle values of 12.86°, 13.58°, 15.58°, 17.64°, 18.42°, 21.56°, 22.90°, 23.70°, 24.64°.

Formula I

2. The hydrogen sulfate crystalline form II of the compound of formula I according to the claim 1, characterized in that it provides characteristic infrared absorption peaks at wavenumbers (/cm$^{-1}$) of 2509, 1751, 1254, 1190, 1154, 1058, 869, 777 and 567; it has a peak value of the differential scanning calorimetry chart at 179.3° C., and melting enthalpy of 89.2 J/g.

3. The hydrogen sulfate crystalline form II of the compound of formula I according to the claim 1, characterized in that the deuterium atom abundance of the deuterated methyl group is not less than 50%.

4. The hydrogen sulfate crystalline form II of the compound of formula I according to the claim 1, characterized in that it provides an X-ray powder diffraction pattern as showed in FIG. 4; it provides an infrared absorption spectrum as showed in FIG. 5.

5. A method for preparing hydrogen sulfate crystalline form II of the compound of formula I of claim 1 comprising: adding the compound of formula I to acetone; stirring to dissolve; cooled in an ice bath and dropwise adding sulfuric acid; crystallization while stirring, removing hydrogen sulfate crystalline form I of the compound of formula I by filtering; resting filtrate under 10° C. for more than one month and separating precipitated crystals.

6. The hydrogen sulfate crystalline form II of the compound of formula I according to the claim 1, characterized in that it includes the following preparation steps: adding the compound of formula I to a ketonic solvent or a ketonic solvent combination of one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve; adding sulfuric acid; heating to reflux and keeping refluxing, crystals precipitated gradually; cooling down while stirring; separating crystals.

7. The hydrogen sulfate crystalline form II of the compound of formula I according to the claim 1, characterized in that it includes the following preparation steps: adding the compound of formula I to a ketonic solvent or a ketonic solvent combination of one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve; adding sulfuric acid; heating to reflux and keeping refluxing, crystals precipitated gradually; removing portion of solvents by distillation; cooling down while stirring; separating crystals.

8. The hydrogen sulfate crystalline form II of the compound of formula I according to the claim 1, characterized in that it includes the following preparation steps: adding the compound of formula I to a ketonic solvent or a ketonic solvent combination of one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve; adding sulfuric acid; adding crystal seeds of the hydrogen sulfate crystalline form II of the compound of formula I; stirring and crystals precipitated gradually; separating crystals.

9. The hydrogen sulfate crystalline form II of the compound of formula I according to the claim 1, characterized in that it includes the following preparation steps: adding the compound of formula I to a ketonic solvent or a ketonic solvent combination of one or more solvent(s) selected from acetone, methyl ethyl ketone, 2-pentanone, 3-pentanone, 3-methyl methyl ethyl ketone, 3,3-dimethyl methyl ethyl ketone, cyclopentanone and/or cyclohexanone, stirring to dissolve; adding sulfuric acid; adding crystal seeds of the hydrogen sulfate crystalline form II of the compound of formula I; stirring and crystals precipitated gradually; removing portion of solvents by distillation; cooling and stirring; separating crystals.

10. The hydrogen sulfate crystalline form II of the compound of formula I according to the claim 1, characterized in that the deuterium atom abundance of the deuterated methyl group is not less than 70%.

11. The hydrogen sulfate crystalline form II of the compound of formula I according to the claim 1, characterized in that the deuterium atom abundance of the deuterated methyl group is not less than 90%.

* * * * *